United States Patent
Taguchi et al.

(10) Patent No.: US 7,145,983 B2
(45) Date of Patent: Dec. 5, 2006

(54) X-RAY ANALYSIS APPARATUS

(75) Inventors: Takeyoshi Taguchi, Tachikawa (JP); Takeo Tajima, Akiruno (JP)

(73) Assignee: Rigaku Corporation, Akishima (JP)

( * ) Notice: Subject to any disclaimer, the term of this patent is extended or adjusted under 35 U.S.C. 154(b) by 153 days.

(21) Appl. No.: 10/911,564

(22) Filed: Aug. 5, 2004

(65) Prior Publication Data

US 2005/0058247 A1    Mar. 17, 2005

(30) Foreign Application Priority Data

Sep. 17, 2003 (JP) .............................. 2003-324609

(51) Int. Cl.
G01N 23/20 (2006.01)

(52) U.S. Cl. ..................... 378/71; 378/70; 378/81; 378/98.8

(58) Field of Classification Search ............ 378/70–81, 378/98.8; 250/370.09
See application file for complete search history.

(56) References Cited

U.S. PATENT DOCUMENTS

| 5,742,658 A | 4/1998 | Tiffin et al. | |
|---|---|---|---|
| 6,198,796 B1* | 3/2001 | Yokoyama et al. | ........... 378/73 |
| 2002/0053641 A1 | 5/2002 | Verbruggen | |
| 2005/0084065 A1* | 4/2005 | Taguchi | ........... 378/70 |

FOREIGN PATENT DOCUMENTS

| EP | 0 997 779 A1 | 5/2000 |
|---|---|---|
| JP | 2002-250705 | 9/2002 |

* cited by examiner

*Primary Examiner*—Edward J. Glick
*Assistant Examiner*—Jurie Yun
(74) *Attorney, Agent, or Firm*—Buchanan Ingersoll & Rooney PC

(57) ABSTRACT

An X-ray analysis apparatus is disclosed, in which X-rays emitted from an X-ray source are applied to a sample and a two-dimensional CCD sensor detects the X-rays diffracted by the sample. The X-ray analysis apparatus has a 2θ-rotation drive and a program. The 2θ-rotation drive moves the two-dimensional CCD sensor. The program is executed to control the motion of the CCD sensor. The 2θ-rotation drive rotates the CCD sensor around ω-axis that extends over the surface of the sample. The program synchronizes the transfer of charges in the CCD sensor with the motion of the CCD sensor driven by the 2θ-rotation drive. Hence, data items for the same diffraction angle can be accumulated in the pixels of the two-dimensional CCD sensor. This achieves high-speed and high-sensitivity in detection of diffracted X-rays.

12 Claims, 7 Drawing Sheets

(FT-TYPE)

(IT – TYPE)

X-RAY ANALYSIS APPARATUS

BACKGROUND OF THE INVENTION

1. Field of the Invention

The present invention relates to an X-ray analysis apparatus in which X-rays emitted from an X-ray source are applied to a sample and a semiconductor X-ray detecting means detects the X-rays diffracted by the sample.

2. Description of the Related Art

In general, X-ray analysis apparatuses have an X-ray generating unit and an X-ray detector. The X-ray generating unit applies an X-ray to a sample. The X-ray detector detects the X-ray that is emerging from the sample. In the X-ray analysis apparatus, the sample diffracts an X-ray applied to it at a specific angle. The X-ray diffracted emerges from the sample. The X-ray, thus diffracted, is detected by the X-ray detector.

Various types of X-ray detectors are known, such as zero-dimensional X-ray detector, one-dimensional X-ray detector, and two-dimensional X-ray detector. These X-ray detectors are also known as zero-dimensional counter, one-dimensional counter and two-dimensional counter, respectively.

The zero-dimensional X-ray detector is an X-ray detector that is configured to detect X-rays as points. Examples of zero-dimensional X-ray detectors, known in the art, are PC (Proportional Counter) and SC (Scintillation Counter).

The one-dimensional X-ray detector is an X-ray detector that is configured to detect X-rays as lines. Examples of one-dimensional X-ray detectors, known in the art, are PSPC (Position Sensitive Proportional Counter) and one-dimensional CCD (Charge-Coupled Device) sensor. The PSPC has a linear signal line which generates an electric signal at the position where an X-ray is applied. The CCD sensor has a plurality of CCD elements arranged in a row.

The two-dimensional X-ray detector is an X-ray detector that is configured to detect X-rays in a plane. Examples of two-dimensional X-ray detectors, known in the art, are those known as imaging plate and two-dimensional CCD sensor. The imaging plate is a detector plate that has an X-ray receiving surface coated with storage phosphor. The two-dimensional CCD sensor has a plurality of CCD elements arranged in rows and columns.

The CCD sensor described above is one of semiconductor position sensors. In recent years, various X-ray analysis apparatuses have been proposed, each comprising a semiconductor position sensor. Such an X-ray analysis apparatus is disclosed in Japanese Patent Laid-Open Publication No. 2002-250705, pp. 4–6, FIG. 2. It is expected that X-ray analysis apparatuses of this type analyze X-rays faster than the zero-dimensional counter and the one-dimensional counter.

In the conventional X-ray analysis apparatus that has a two-dimensional CCD sensor, X-rays are detected while the sample (i.e., object of analysis) and the two-dimensional CCD sensor are moving relative to each other. The apparatus can hardly detect X-rays at high speed or high sensitivity. This is because the CCD pixels cannot receive X-rays at high resolution when the sample and the two-dimensional CCD sensor move relative to each other at an excessively high speed.

SUMMARY OF THE INVENTION

The present invention has been made in view of the foregoing. An object of this invention is to provide an X-ray analysis apparatus which has a semiconductor X-ray detector such as a two-dimensional CCD sensor and which can analyze X-rays at high speed and high accuracy.

An X-ray analysis apparatus according to the invention is of the type in which X-rays emitted from an X-ray source are applied to a sample and a semiconductor X-ray detecting means detects the X-rays diffracted by the sample. The apparatus comprises:

a detector-moving means for moving the semiconductor X-ray detecting means with respect to the sample to enable the semiconductor X-ray detecting means to detect the X-rays; and a charge-transfer signal generating means for generating a charge-transfer signal in the semiconductor X-ray detecting means, every time the semiconductor X-ray detecting means is moved for a distance corresponding to the width of the pixels that constitute the semiconductor X-ray detecting means.

The term "charge-transfer signal" means a signal instructing that electric charges be transferred. Generally, it is a pulse signal that has a frequency of about 1 MHz.

In the X-ray analysis apparatus, the semiconductor X-ray detecting means, such as a two-dimensional CCD sensor, is driven around the sample by the detector-moving means. The semiconductor X-ray detecting means can therefore detect X-rays that travel after diffracted by the sample at various diffraction angles. Since the transfer of charges in the semiconductor X-ray detector are synchronized with the motion of the semiconductor X-ray detecting means, each of the pixels of the semiconductor X-ray detecting means can accumulate the energies of X-rays diffracted at the same angle. Hence, even when the semiconductor X-ray detecting means moves at high speed, each pixel can accurately measure the intensity of the X-ray diffracted at each angle. This can accomplish an X-ray analysis of the sample, at a very high speed and a high sensitivity.

It is desired that the semiconductor X-ray detecting means used in the present invention be a CCD sensor. The CCD sensor has a CCD (Charge-Coupled Device) that transfers electric charges from potential wells to other potential wells. The region corresponding to one potential well is one pixel. The potential wells are arranged in a one-dimensional pattern (that is, in a line), or in a two-dimensional pattern (that is, in a plane). To detect X-rays at high speed and high sensitivity, it is desirable to arrange the pixels in a two-dimensional pattern.

The potential wells are provided in, for example, such a MOS (Metal Oxide Semiconductor) structure as shown in FIG. 6. The MOS structure comprises metal electrodes 1, an oxide insulating layer 2, and a semiconductor layer 3. More specifically, a potential well is formed when a voltage is applied to one of the electrodes 1, while a different voltage is applied to the other electrodes 1, thus setting that part of the layer 3 which lies beneath this electrode 1, at a particular potential, and setting the other parts of the layer 3 at a different potential. The signal charge confined in the potential well is transferred through the semiconductor layer 3 to the output unit.

A method of detecting X-rays by using a CCD sensor has been known. In this method, a phosphor plate is interposed between the CCD sensor and the sample. The X-rays emerging from the sample are applied to the phosphor plate, which emits light from the parts irradiated with the X-rays. The CCD sensor receives the light. By contrast, the semiconductor X-ray detecting means used in the present invention can directly detect X-rays, not through a phosphor plate.

Further, the semiconductor X-ray detecting means generates electrons the number of which is proportional to the photon energy it has received.

The CCD sensor used as semiconductor X-ray detecting means in this invention may be a one-dimensional one or a two-dimensional one. Nonetheless, a two-dimensional CCD sensor is preferable. Various types of two-dimensional CCD sensors are available, such as FT (Frame Transfer) type, FFT (Full Frame Transfer) type, IT (Interline Transfer) type, and the like.

These types of two-dimensional CCD sensors will be described, using the terms "horizontal retrace period" and "vertical retrace period." These terms are generally used in explaining the process of reading and writing one-frame video data by scanning the reading point. As shown in FIG. 7, the horizontal retrace period is a time during which the reading point moves from one horizontal scanning line $S_H$ to the next horizontal scanning line $S_H$. The vertical retrace period is a time between one vertical scanning to the next. In other words, during this period, the reading point moves from the ending point $P_E$ of one frame to the starting point $P_S$ of the next frame.

As FIG. 3 shows, a two-dimensional CCD sensor of FT type has a light-receiving unit 6, a charge-accumulating unit 7, a horizontal shift register 8, and an output unit 9. The light-receiving unit 6 is a vertical shift register. The charge-accumulating unit 7 is a vertical shift register, too. Vertical shift registers are known also as "parallel registers." Horizontal shift registers are known also as "serial registers" or "reading registers." The light-receiving unit 6 has metal electrodes of the same type as the electrodes 1 (see FIG. 6). The metal electrodes are made of transparent conductive material such as polysilicon.

When light is applied to the semiconductor layer 3 through the metal electrodes 1, photoelectric conversion is performed, generating signal charges. The signal charges are accumulated in the potential well lying beneath the electrodes 1. The signal charges are transferred in units of frames, at high speed to the charge-accumulating unit 7 during the vertical retrace period, i.e., the period between one vertical scanning and the next vertical scanning. Thus, in the FT-type CCD sensor, the light-receiving unit 6, which is a vertical shift register, functions as a photoelectric converter during the signal-accumulating period. While the photoelectric conversion is going on by the light-receiving unit 6, thus accumulating signals, the signal charges are transferred from the charge-accumulating unit 7 to the horizontal shift register 8, in units of lines, during the horizontal retrace period, i.e., the period between one horizontal scanning and the next horizontal scanning.

As FIG. 4 shows, a two-dimensional CCD sensor of FFT type has basically the same configuration as the FT-type CCD sensor of FIG. 3, but does not have charge-accumulating unit 7. Without a charge-accumulating unit 7, the FFT-type CCD sensor usually has a shutter mechanism at the light-receiving unit 6. In the FFT-type CCD sensor, charges are accumulated in the potential wells (i.e., pixels) of the light-receiving unit 6 during the signal-accumulating period. While the shutter mechanism remains closed, the signal charges are transferred to the output unit 9 via the horizontal shift register 8. Having no charge-accumulating units, the FFT-type CCD sensor can have more pixels than the FT-type CCD sensor if it has the same size as the FT-type CCD sensor. Alternatively, its light-receiving unit 6 may have a larger area.

As FIG. 5 depicts, a CCD sensor of IT type has a light-receiving unit 6, vertical shift registers 7, transfer gates 11, a horizontal shift register 8, and an output unit 9. The light-receiving unit 6 has photodiodes 6a arranged in rows. The vertical shift registers 7 are arranged to sandwich the photodiode 6a. Each transfer gate 11, which operate as a switch, is provided between a row of the photodiodes 6a and a shift register 7. Each photodiode 6a performs photoelectric conversion, generating a signal charge. The signal charge generated by the photodiode 6a is accumulated in the coupling capacitor provided in the photodiode 6a. The signal charge is transferred from the photodiode 6a to the vertical shift register 7 via the transfer gate 11 during the vertical retrace period. The signal charges are transferred from the photodiodes 6a to the vertical shift registers 7 at the same time, unlike in the FT-type CCD sensor (see FIG. 3). Thereafter, the signal charges are transferred to the horizontal shift register 8, in units of lines during the horizontal retrace period. They are ultimately output from the horizontal shift register 8 to the output unit 9.

It is desired that the X-ray analysis apparatus of this invention should have a θ-rotation means and a 2θ-rotation means. The θ-rotation means rotates the X-ray source or the sample, thereby to change an angle at which an X-ray is applied to the sample. The 2θ-rotation means rotates the semiconductor X-ray detecting means around the sample, thereby to detect the X-ray diffracted by the sample. In this case, the charge-transfer signal generating means should generate a charge-transfer signal in the semiconductor X-ray detecting means, every time the 2θ-rotation means moves the semiconductor X-ray detecting means for a distance that corresponds to the width of every pixel of the semiconductor X-ray detecting means. Thus configured, the analysis apparatus is fit to analyze the crystal structure or the like of sample powder, by utilizing the diffraction of X-rays.

It is desired that the X-ray analysis apparatus of this invention should have an arithmetic operating means for arithmetically producing two-dimensional diffraction-image data representing a band-shaped image, from signals output from the semiconductor X-ray detecting means. The band-shaped image is such a two-dimensional diffraction image 'K' as shown in FIG. 2, indicating at which diffraction angle (2θ) a diffracted X-rays has emerged from the sample and how intense the X-ray is. In this two-dimensional diffraction image, the diffraction angle is plotted on the x-axis (i.e., the lateral axis), and the position above or below the optical axis of the X-ray (or central axis) applied to the sample is plotted on the y-axis (i.e., the longitudinal axis). When the semiconductor X-ray detecting means receives an X-ray, the X-ray is plotted in the two-dimensional diffraction image, as a point at the corresponding 2θ position and at a position above or below its optical axis. Hence, if many X-rays (or a very intense X-ray) are applied at the same 2θ position, an image having a high dot density will be formed. Thus, the intensities of X-rays can be determined from the density of the image, i.e., the color density of the image. A display, particularly a color display, such as a CRT (Cathode Ray Tube) or a LCD (Liquid Crystal Display) may be used to display the two-dimensional diffraction image. In this case, the parts of the image displayed have different colors that correspond to the dot densities. This makes it easy for the user to analyze the two-dimensional diffraction image.

The two-dimensional diffraction image is thus obtained by using the semiconductor X-ray detecting means. Instead, it can be obtained by using a two-dimensional image detecting plate having a phosphor layer that can store energy. If this is the case, the two-dimensional image detecting plate stores a latent image of energy in any part irradiated with an X-ray. When a laser beam or the like is applied to the plate, any part storing the latent image of energy emits light. This light may be detected by a photoelectric tube or the like. The intensity of any X-ray that has contributed to form the latent image of energy can then be determined.

In the X-ray analysis apparatus having a two-dimensional image detecting plate, a laser beam or the like must be applied to the plate after the plate has been exposed to X-rays, in order to determine the intensity of each X-ray. The intensity of each X-ray cannot be accurately determined if errors are made in reading the light emitted from the plate. On the contrary, in this invention, the semiconductor X-ray detecting means obtains a two-dimensional diffraction image, from which the sample can be analyzed at high precision.

The X-ray analysis apparatus according to this invention may have an arithmetic operating means for arithmetically producing diffraction-profile data from the signals output from the semiconductor X-ray detecting means, in addition to the arithmetic operating means for arithmetically producing the two-dimensional diffraction-image data. The diffraction-profile represents such a diffraction profile 'F' as shown in FIG. 2. The profile 'F' is a graph that indicates at which diffraction angle (2θ) a diffracted X-rays has emerged from the sample and how intense the X-ray is. In the diffraction profile, the diffraction angle (2θ) is plotted on the x-axis (i.e., the lateral axis), and the position above or below the optical axis of the X-ray applied to the sample is plotted on the y-axis (i.e., the longitudinal axis). This diffraction profile is of the same type as obtained by a conventional X-ray diffraction apparatus that has a zero-dimensional counter such as a scintillation counter (SC).

It is desired that the X-ray analysis apparatus, having the arithmetic operating means for arithmetically producing the two-dimensional diffraction-image data and the arithmetic operating means for arithmetically producing diffraction-profile data, should further comprise a display means for simultaneously displaying the two-dimensional diffraction image and the diffraction profile on a screen. The display means may be a video display means such as a CRT or an LCD, or a printing means such as a printer that prints images on a recording medium such as paper sheets.

DETAILED DESCRIPTION OF THE PREFERRED EMBODIMENTS

An embodiment of the present invention will be described, with reference to the accompanying drawings. The embodiment is an X-ray diffraction apparatus, which is a type of an X-ray analysis apparatus that can be effectively used to analyze samples in the form of powder. Needless to say, this invention is not limited to this embodiment.

Figure 1:
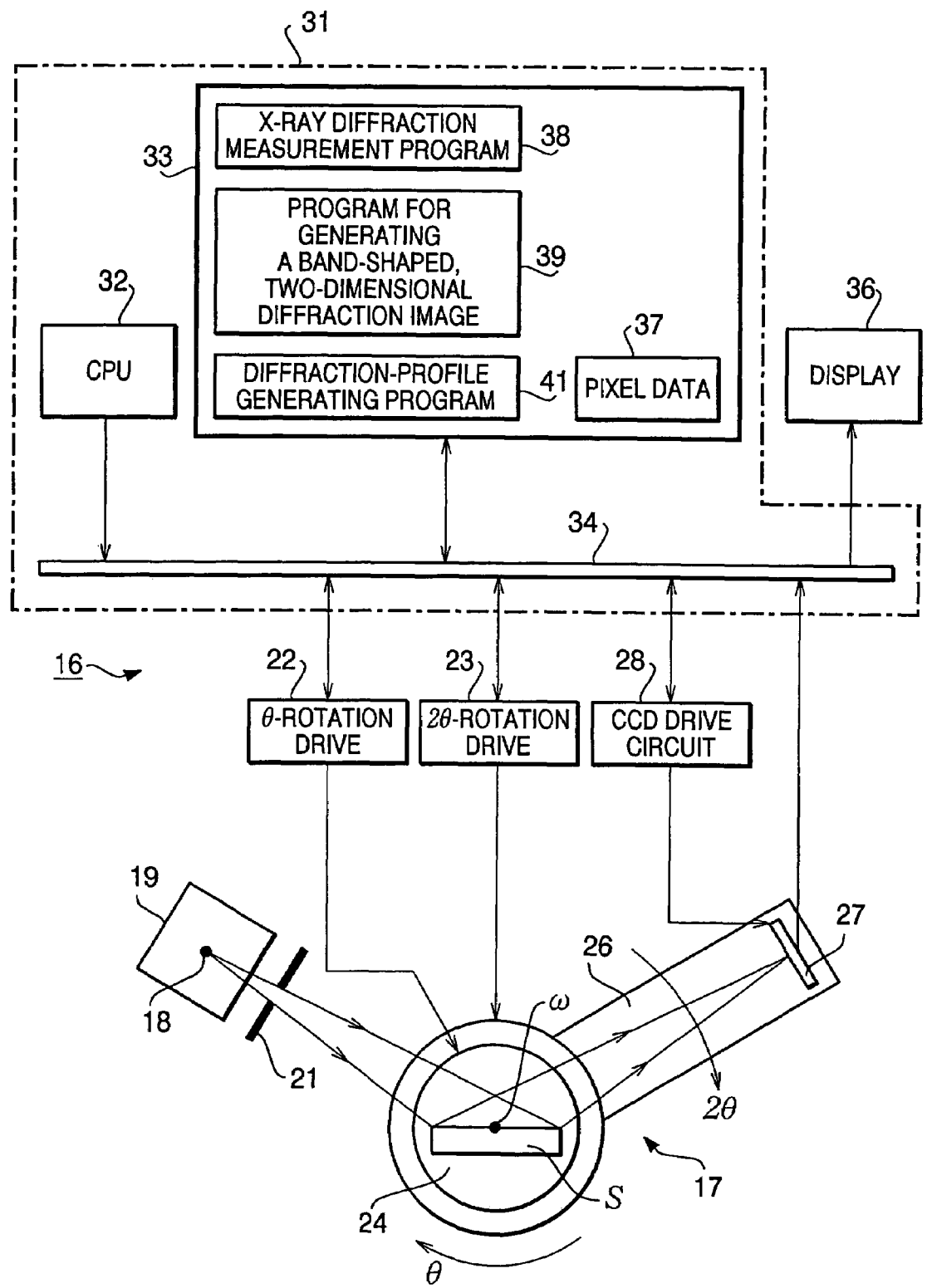
FIG. 1 is a diagram showing an embodiment of the X-ray analysis apparatus according to the present invention.

FIG. 1 shows an X-ray diffraction apparatus 16 that is an X-ray analysis apparatus according to the invention. The X-ray diffraction apparatus 16 has an X-ray generator 19, a diversion-controlling slit 21, and a goniometer 17. The X-ray generator 19 incorporates an X-ray focal point 18 which serves as an X-ray source. The slit 21 controls the diversion of the X-ray emitted from the X-ray generator 19 and guides the X-ray to a sample 'S'. The goniometer 17 is a device that determines the direction in which the X-ray is coming from the X-ray generator 19 through the diversion-controlling slit 21. The goniometer 17 has a θ-rotation unit 24 and a 2θ-rotation unit 26. The θ-rotation unit 24 holds the sample 'S'. The 2θ-rotation unit 26 holds a two-dimensional CCD sensor 27, which is used as semiconductor X-ray detecting means.

Driven by a θ-rotation drive 22, the θ-rotation unit 24 rotates the sample 'S' around ω-axis. Hereinafter, the rotation of the sample 'S' will be referred to as "θ-rotation." The ω-axis is a line passes over the X-ray incidence surface of the sample 'S' and extends perpendicular to the plane of FIG. 1. Driven by a 2θ-rotation drive 23, the 2θ-rotation unit 26 rotates the CCD sensor 27 around the ω-axis. Hereinafter, the rotation of the CCD sensor 27 will be referred to as "2θ-rotation." The 2θ-rotation is performed in the same direction as the θ-rotation, at an angular velocity that is twice as high as that of the θ-rotation.

Figure 4:
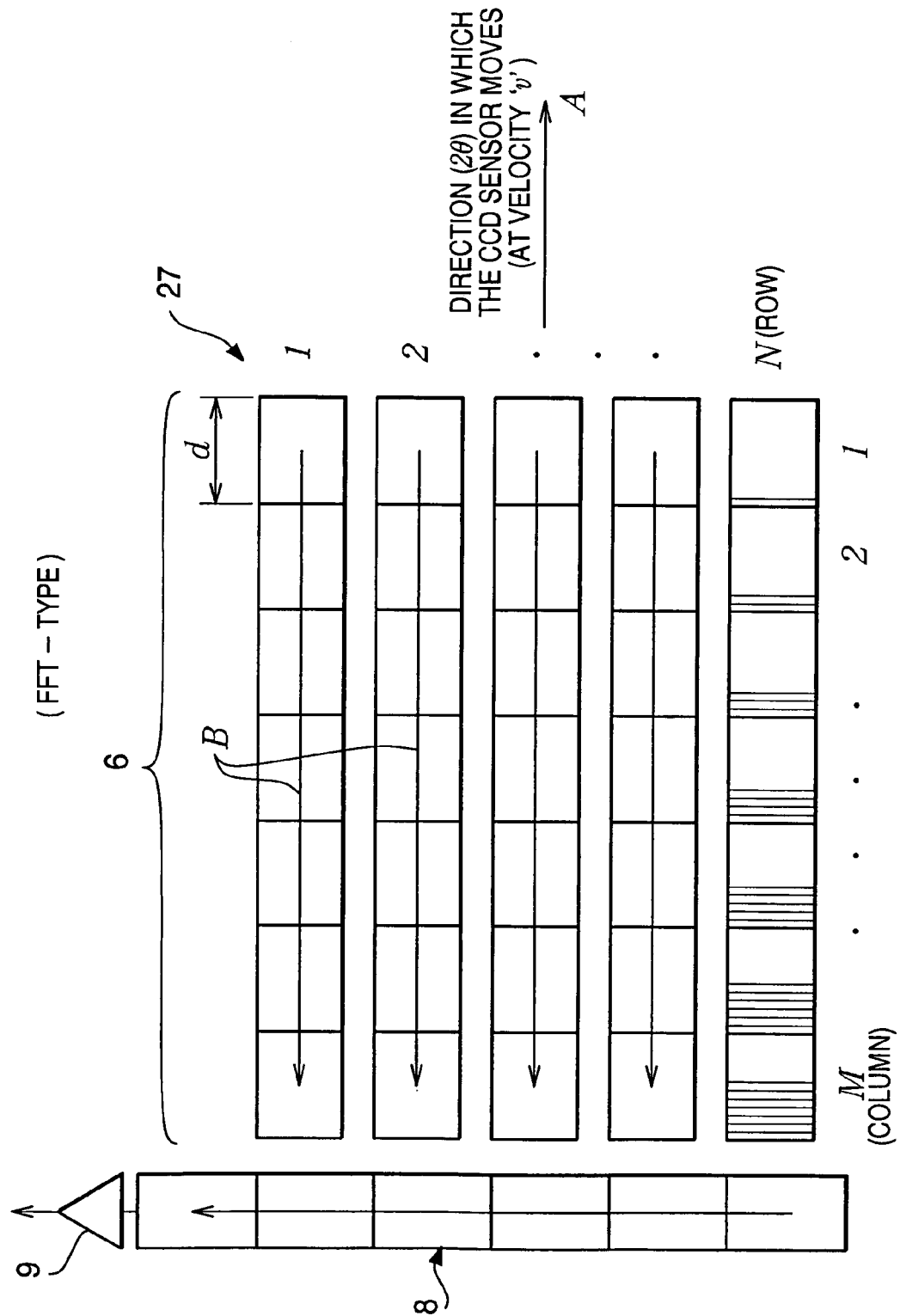
FIG. 4 is a schematic representation of another type of a CCD sensor that can be incorporated in the apparatus of FIG. 1.
Figure 5:
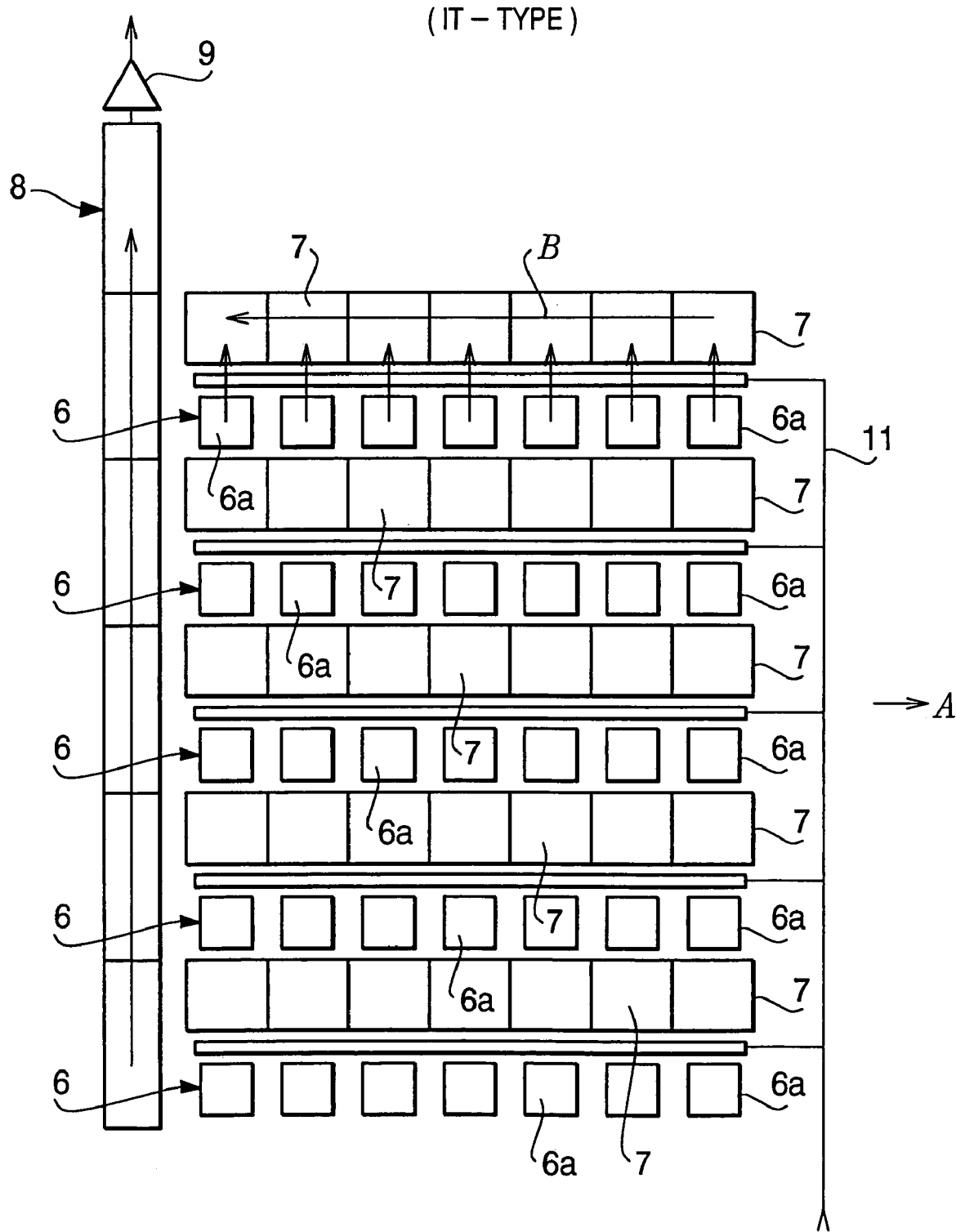
FIG. 5 is a schematic representation of still another type of a CCD sensor that can be incorporated in the apparatus of FIG. 1.
Figure 6:
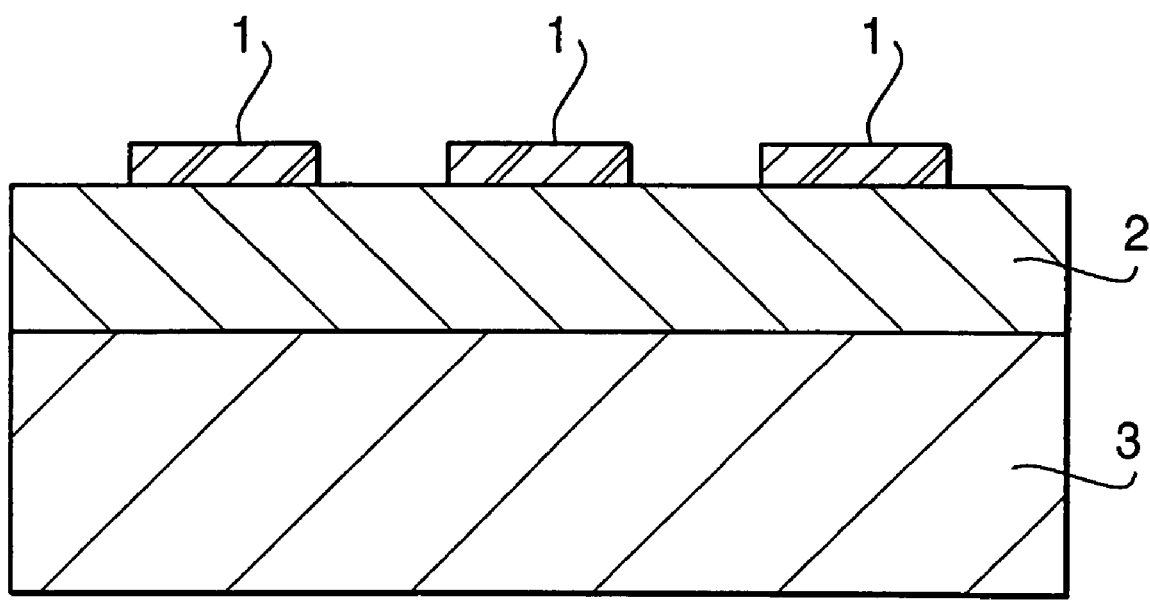
FIG. 6 is a cross sectional view of a CCD sensor, depicting some of the pixels of the CCD sensor.
Figure 7:
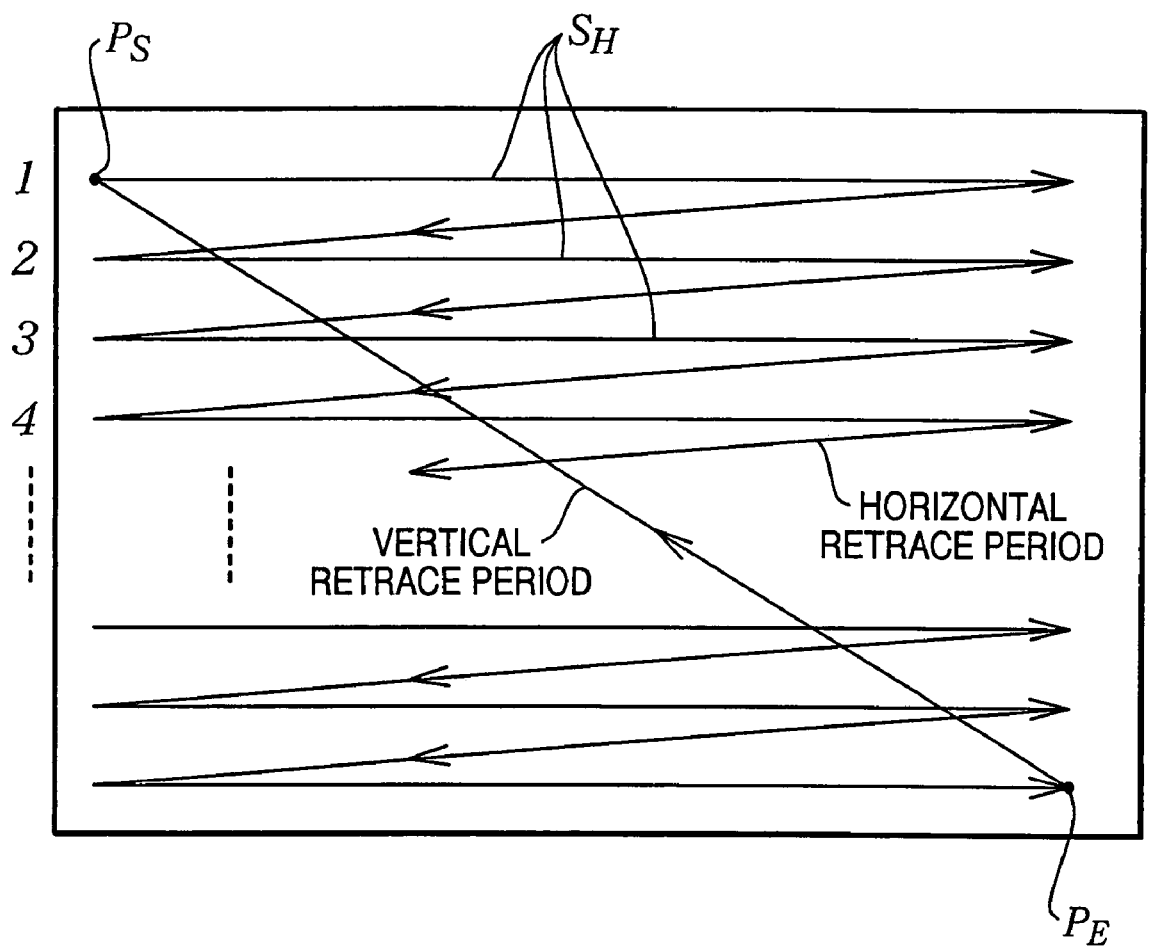
FIG. 7 is a diagram for explaining the function of a CCD sensor.

In this embodiment, the two-dimensional CCD sensor 27 is an FFT-type CCD sensor that is illustrated in FIG. 4. It is driven by a CCD drive circuit 28 as is illustrated in FIG. 1. The CCD drive circuit 28 performs so-called TDI (Time Delay Integration) to drive the two-dimensional CCD sensor 27.

The X-ray diffraction apparatus 16 has a controller 31. The controller 31 incorporates a CPU (Central Processing Unit) 32, a storage medium, or memory 33, and a bus 34 for transferring various signals. The memory 33 is a semiconductor memory such as a ROM (Read-Only Memory) or a RAM (Random-Access Memory), a mechanical memory such as a hard disk, a CD (Compact Disc) or an MO (Magnetic Optical) disk, or a memory of any other type. The X-ray diffraction apparatus 16 further has a display 36. The display 36 is a video display means such as a CRT or an LCD, or a printing means such as a printer.

The memory 33 includes four files 37, 38, 39 and 41. The file 37 stores the pixel data output from the CCD sensor 27. The file 38 is the program that is used to perform X-ray diffraction analysis. The file 39 is the program that is used to generate a band-shaped, two-dimensional diffraction image 'K' shown in FIG. 2 from the pixel data stored in the pixel-data file 37. The file 41 is the program for generating a diffraction profile 'F' shown in FIG. 2 from the pixel data stored in the file 37.

The X-ray diffraction analysis program 38 controls the θ-rotation drive 22 and the 2θ-rotation drive 23. More precisely, the X-ray diffraction analysis program 38 makes the drive 22 rotate the θ-rotation unit 24 holding the sample 'S' around the ω-axis, thus rotating the sample 'S' at a prescribed angular velocity. In other words, the θ-rotation drive 22 achieves the θ-rotation of the sample 'S'. As the sample 'S' undergoes the θ-rotation, the incidence angle at which the X-ray is applied from the X-ray focal point 18 to the sample 'S' is changed. The X-ray diffraction analysis program 38 controls the 2θ-rotation unit 26, which rotates the CCD sensor 27 around the ω-axis in the same direction as the sample 'S' that undergoes the θ-rotation, at an angular velocity that is twice as high as that of the θ-rotation. So rotated, the CCD sensor 27 can detect the X-ray diffracted by the sample 'S'.

The sample 'S' may not be subjected to the θ-rotation. In this case, the X-ray generator 19 and the diversion-controlling slit 21 are rotated around the ω-axis, thus undergoing the θ-rotation. At the same time, the CCD sensor 27 is subjected to the 2θ-rotation in the opposite direction. This brings forth the same result as obtained by subjecting the sample 'S' to the θ-rotation.

In the present embodiment, the X-ray diffraction analysis program 38 gives instructions to the CCD drive circuit 28, which drives the CCD sensor 27. Thus driven, the CCD sensor 27 performs TDI (Time Delay Integration). To make the CCD sensor 27 perform TDI, the X-ray diffraction analysis program 38 serves to transfer the electric charge in the CCD sensor 27 at the same velocity as the angular velocity of the CCD sensor 27 that is undergoing the 2θ-rotation performed by the 2θ-rotation drive 23.

Now, TDI will be explained. TDI is performed on the assumption that the FFT-type CCD sensor of FIG. 4 is employed. This CCD sensor is moved at a constant speed 'v' in the direction of arrow 'A' shown in FIG. 4. The pulse signal used to transfer the electric charge in the CCD sensor has frequency 'f'. Assume that the electric charge moves in the direction of arrow 'B', i.e., the direction opposite to the direction of the arrow 'A' in which the CCD sensor is moved. The pixels of the CCD sensor have a width 'd'. The transfer of electric charge is synchronized with the motion of the CCD sensor, thus establishing the following equation:

$$v = f \times d$$

As can be seen from FIG. 4, the input at the first column of the 'M' columns (i.e., the rightmost column) moves to the second column upon lapse of time 1/f as the CCD sensor 27 moves at velocity 'v' in the direction of the arrow 'A'. Simultaneously, the charge at the first column is transferred to the second column. The charge is thus accumulated in the second column by virtue of photoelectric conversion. The sequence of these operations is repeated until the electric charge reaches the last column (i.e., 'M'th column). As a result, signal charge 'M' times as much as is possible with the ordinary charge-transfer not using TDI can be accumulated during this period. The signal charge, thus accumulated, is continuously output, in units of columns, from the horizontal shift register 8 that is provided in the CCD sensor. The signal charges thus output represent a two-dimensional image. As can be understood from this, TDI helps to detect weak diffracted X-rays.

In the X-ray analysis apparatus according to the present embodiment, which is configured as described above, as shown in FIG. 1, the sample 'S' is subjected to the θ-rotation at the start of the X-ray diffraction analysis. At the same time, the CCD sensor 27 is put to the 2θ-rotation. Further, an X-ray is applied from the X-ray focal point 18 to the sample 'S'. While the incidence angle of the X-ray to the sample 'S' is changing as the θ-rotation proceeds, there may be timing when Bragg condition of diffraction is satisfied. At this time, a diffracted X-ray emerges from the sample 'S'. The diffracted X-ray travels in the direction at a specific diffraction angle (2θ). One of the pixels provided in the light-receiving unit 6 of the CCD sensor 27 shown in FIG. 4 receives the diffracted X-ray. Upon receipt of the X-ray, this pixel generates an electric charge, which is accumulated in the CCD sensor 27.

The CCD sensor 27 performs TDI and transfers the electric charge in synchronism with its 2θ-rotation. Hence, the signal charge relating to the same diffraction angle (2θ) is accumulated in one pixel and then in the next pixel. The CCD sensor 27 can always store the correct data about the diffracted X-ray in the pixel even if it is moved at a high speed. The signal charge thus stored in each pixel is transferred from the light-receiving unit 6 to the horizontal shift register 8, in unit of columns. The charge is then stored into the pixel-data file 37 shown in FIG. 1 through an output unit 9. This acquisition of data terminates when the CCD sensor 27 shown in FIG. 1 finishes scanning the sample 'S' over a desired range of diffraction angle, for example, 20° to 100°. Thus, the data representing the intensities of X-rays diffracted within this range of diffraction angle is stored into the pixel-data file 37.

The CPU 32 executes the program stored in the file 39 shown in FIG. 1, generating (i.e., arithmetically producing) data that represents a two-dimensional diffraction image 'K', from the pixel data 37 obtained. Further, the CPU 32 executes the diffraction-profile generating program 41 shown in FIG. 1, generating (i.e., arithmetically producing) diffraction profile 'F' shown in FIG. 2 from the pixel data 37 obtained. The generated two-dimensional diffraction image 'K' and the diffraction profile 'F' are displayed on a screen as an image or character by the display 36 shown in FIG. 1, whenever necessary. The display 36 may display, on its screen, either the image 'K' or the profile 'F', or both at the same time. If both image 'K' and profile 'F' are displayed, an observer can compare them. Thus, the observer can analyze the sample 'S' accurately and quickly.

Figure 2:
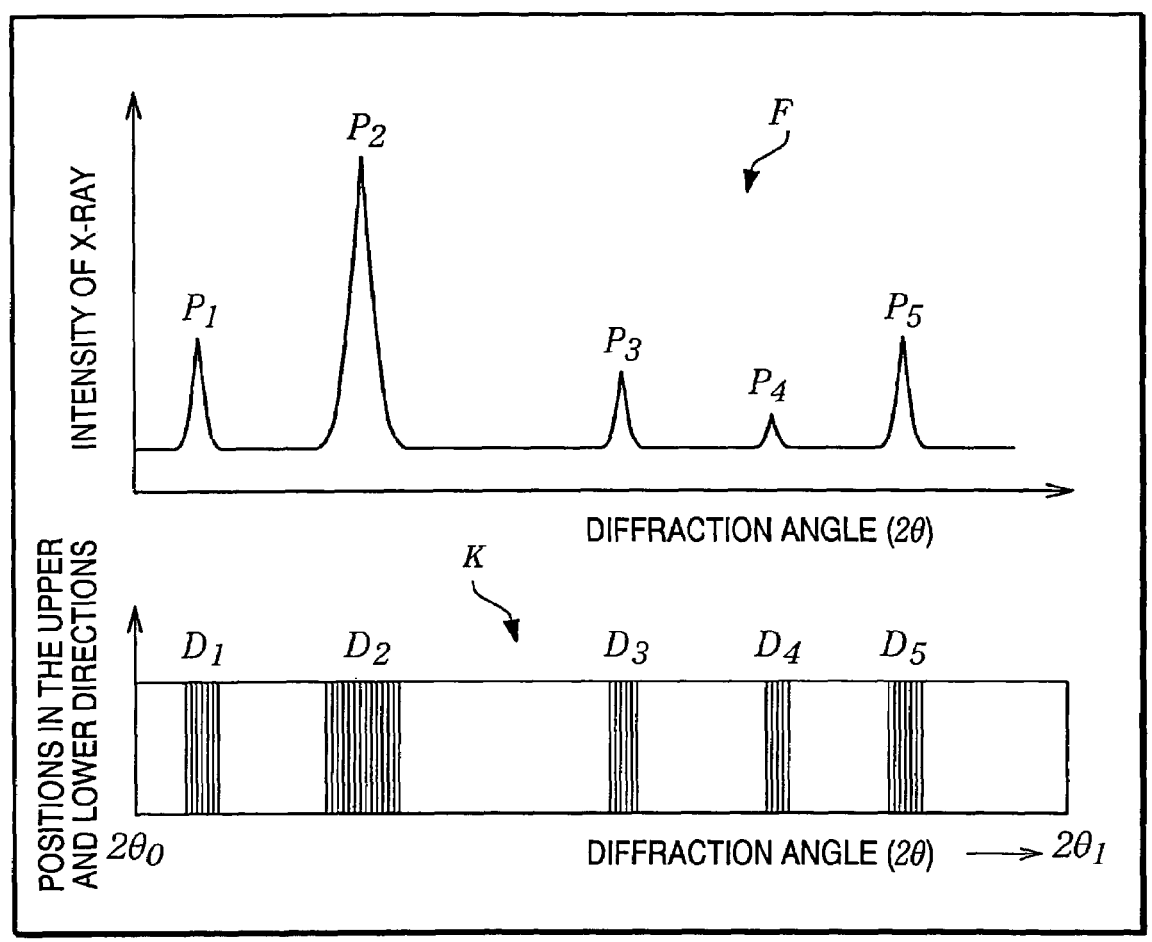
FIG. 2 is a diagram illustrating an example of analysis obtained by using the apparatus shown in FIG. 1.
Figure 3:
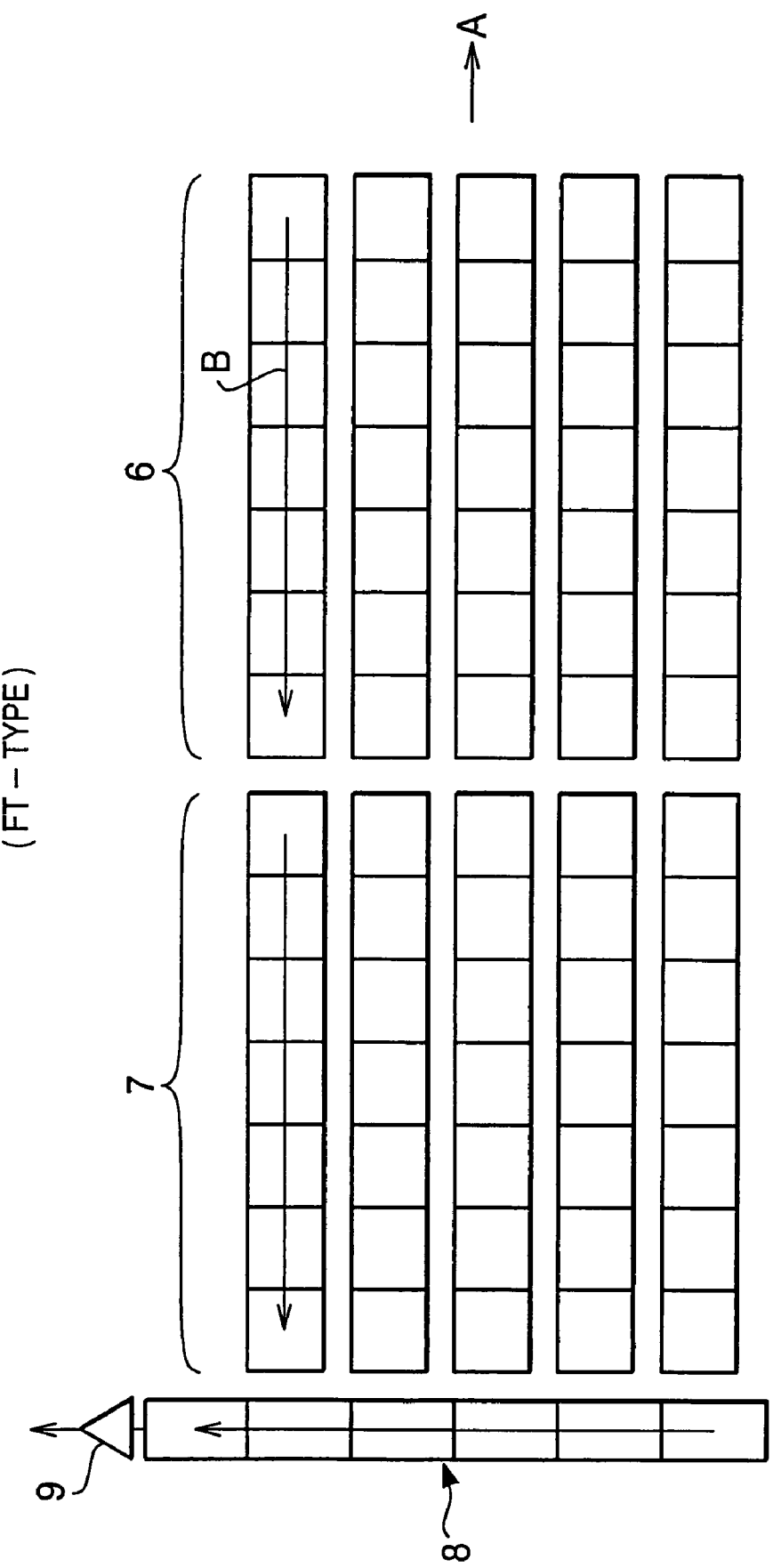
FIG. 3 is a schematic representation of a type of a CCD sensor that can be incorporated in the apparatus of FIG. 1.

Diffraction-image data items D1, D2, D3, . . . that constitute the two-dimensional diffraction image 'K' shown in FIG. 2 correspond to peaks P1, P2, P3, . . . of the waveform (i.e., the diffraction profile 'F'), respectively. The image density of, for example, data item D1 represents the intensity of the X-ray detected. The height of, for example, peak P1, represents the intensity of the X-ray detected, too. The CPU 32 shown in FIG. 1 can generate a two-dimensional diffraction image 'K' (FIG. 2), in which diffraction-data items D1, D2, D3 . . . have different colors, each representing a specific X-ray intensity.

(Modification)

The X-ray diffraction apparatus 16 shown in FIG. 1, which has the two-dimensional CCD sensor 27, can obtain such a diffraction profile 'F' and a two-dimensional diffraction image 'K' as illustrated in FIG. 2. However, the pixels of the CCD sensor 27 may be saturated in terms of energy when they receive extremely intense X-rays diffracted by the sample 'S'. If the pixels are saturated, the apparatus 16 cannot acquire accurate data about the diffracted X-rays. In this case, the CCD sensor 27 may be moved faster, lowering the measured levels of the diffracted X-rays. Then, the saturation of the pixels can be prevented. This method, however, may reduce the sensitivity of detecting X-rays of low intensity.

To prevent both the saturation of the pixels which receive high intense X-rays and the reduction of the sensitivity of detecting low intense X-rays, it is desired that the CCD sensor 27 be moved very fast and moved so several times, thereby obtaining several data items about each pixel. For instance, the CCD sensor 27 is moved twice or thrice, each time scanning the sample 'S' through a diffraction angle of 20° to 100°, thereby to generate two or three data items about each pixel. This way of scanning the sample 'S' can not only avoid the failure of detecting weak diffracted X-rays, but also expand the dynamic range, i.e., the range of detecting X-rays. If the moving speed of the CCD sensor 27 is increased, a signal having a proportionally high frequency is generated to transfer the signal charges in the CCD sensor 27.

(Other Embodiments)

A preferred embodiment of the invention has been described. This invention is not limited to the embodiment, nevertheless. Various modifications can be made within the scope of the invention, which will be defined by the claims set forth later.

For example, the CCD sensor 27 that is an FFT-type one used in the embodiment shown in FIG. 1 may be replaced, if necessary, by a CCD sensor of any other configuration. Although the X-ray diffraction apparatus 16 described above is of the θ-2θ type, this invention can be applied to an X-ray diffraction apparatus of any other type. Moreover, the present invention can be applied to any X-ray analysis apparatus other than X-ray diffraction apparatuses.

What is claimed is:

1. An X-ray analysis apparatus in which X-rays emitted from an X-ray source are applied to a sample and semiconductor X-ray detecting means detects the X-rays diffracted by the sample, said apparatus comprising:
    detector-moving means for rotationally moving the semiconductor X-ray detecting means with respect to the sample to enable the semiconductor X-ray detecting means to detect the X-rays; and
    charge-transfer signal generating means for generating a charge-transfer signal in the semiconductor X-ray detecting means, every time the semiconductor X-ray detecting means is moved for a distance corresponding to the width of the pixels that constitute the semiconductor X-ray detecting means.

2. The X-ray analysis apparatus according to claim 1, wherein the semiconductor X-ray detecting means has a CCD that is a device for transferring, in a semiconductor, signal charges accumulated in a plurality of potential wells, which are arranged in rows and columns on an X-ray receiving surface and which constitute pixels.

3. The X-ray analysis apparatus according to claim 2, wherein the semiconductor X-ray detecting means has:
    a parallel shift register which is composed of the pixels arranged in rows and columns on the X-ray receiving surface; and
    a serial shift register in which the signal charges are transferred in units of pixel columns provided in the parallel shift register.

4. The X-ray analysis apparatus according to claim 3, further comprising:
    θ-rotation means for rotating the X-ray source or the sample, thereby to change an angle at which an X-ray is applied to the sample; and
    2θ-rotation means for rotating the semiconductor X-ray detecting means around the sample, thereby to detect the X-ray diffracted by the sample,
    wherein the charge-transfer signal generating means generates a charge-transfer signal in the semiconductor X-ray detecting means, every time the 2θ-rotation means moves the semiconductor X-ray detecting means for a distance that corresponds to the width of every pixel of the semiconductor X-ray detecting means.

5. The X-ray analysis apparatus according to claim 4, further comprising arithmetic operating means for arithmetically producing two-dimensional diffraction-image data representing a band-shaped image, from signals output from the semiconductor X-ray detecting means.

6. The X-ray analysis apparatus according to claim 5, further comprising arithmetic operating means for arithmetically producing diffraction-profile data from the signals output from the semiconductor X-ray detecting means.

7. The X-ray analysis apparatus according to claim 6, further comprising display means for simultaneously displaying the two-dimensional diffraction image and the diffraction profile on a screen.

8. The X-ray analysis apparatus according to claim 1, further comprising:
    θ-rotation means for rotating the X-ray source or the sample, thereby to change an angle at which an X-ray is applied to the sample; and
    2θ-rotation means for rotating the semiconductor X-ray detecting means around the sample, thereby to detect the X-ray diffracted by the sample,
    wherein the charge-transfer signal generating means generates a charge-transfer signal in the semiconductor X-ray detecting means, every time the 2θ-rotation means moves the semiconductor X-ray detecting means for a distance that corresponds to the width of every pixel of the semiconductor X-ray detecting means.

9. The X-ray analysis apparatus according to claim 2, further comprising:
    θ-rotation means for rotating the X-ray source or the sample, thereby to change an angle at which an X-ray is applied to the sample; and
    2θ-rotation means for rotating the semiconductor X-ray detecting means around the sample, thereby to detect the X-ray diffracted by the sample,
    wherein the charge-transfer signal generating means generates a charge-transfer signal in the semiconductor X-ray detecting means, every time the 2θ-rotation means moves the semiconductor X-ray detecting means for a distance that corresponds to the width of every pixel of the semiconductor X-ray detecting means.

10. The X-ray analysis apparatus according to claim 1, further comprising arithmetic operating means for arithmetically producing two-dimensional diffraction-image data representing a band-shaped image, from signals output from the semiconductor X-ray detecting means.

11. The X-ray analysis apparatus according to claim 2, further comprising arithmetic operating means for arithmetically producing two-dimensional diffraction-image data representing a band-shaped image, from signals output from the semiconductor X-ray detecting means.

12. The X-ray analysis apparatus according to claim 3, further comprising arithmetic operating means for arithmetically producing two-dimensional diffraction-image data representing a band-shaped image, from signals output from the semiconductor X-ray detecting means.

* * * * *